US011642033B2

(12) United States Patent
Horng et al.

(10) Patent No.: US 11,642,033 B2
(45) Date of Patent: May 9, 2023

(54) VITAL-SIGN RADAR SENSOR USING WIRELESS INTERNET SIGNALS

(71) Applicant: NATIONAL SUN YAT-SEN UNIVERSITY, Kaohsiung (TW)

(72) Inventors: Tzyy-Sheng Horng, Kaohsiung (TW); Yi-Chen Lai, Kaohsiung (TW); Jui-Yen Lin, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 303 days.

(21) Appl. No.: 17/161,834

(22) Filed: Jan. 29, 2021

(65) Prior Publication Data

US 2022/0192512 A1 Jun. 23, 2022

(30) Foreign Application Priority Data

Dec. 17, 2020 (TW) .................................. 109144803

(51) Int. Cl.
| | | |
|---|---|---|
| *A61B 5/0205* | (2006.01) | |
| *G01S 13/88* | (2006.01) | |
| *G16H 40/67* | (2018.01) | |
| *G01S 7/35* | (2006.01) | |
| *G01S 13/58* | (2006.01) | |

(52) U.S. Cl.
CPC ............ *A61B 5/0205* (2013.01); *G01S 13/88* (2013.01); *G16H 40/67* (2018.01); *G01S 7/352* (2013.01); *G01S 13/583* (2013.01)

(58) Field of Classification Search
CPC .................................. G01S 13/46; G01S 13/74
See application file for complete search history.

(56) References Cited

U.S. PATENT DOCUMENTS

| | | | |
|---|---|---|---|
| 10,101,745 B1 | 10/2018 | Sun et al. | |
| 2006/0250234 A1* | 11/2006 | Maschke | G01S 13/74 340/539.23 |
| 2014/0145873 A1* | 5/2014 | Miller | G01S 13/46 342/146 |
| 2017/0205502 A1* | 7/2017 | Honma | G01S 13/88 |
| 2018/0192919 A1* | 7/2018 | Nakayama | G01S 7/415 |
| 2018/0224526 A1 | 8/2018 | Wang et al. | |
| 2019/0365244 A1 | 12/2019 | Horng et al. | |

(Continued)

FOREIGN PATENT DOCUMENTS

| | | | | | |
|---|---|---|---|---|---|
| CN | 108398680 A | * | 8/2018 | ............. | G01S 7/352 |
| CN | 109239708 A | * | 1/2019 | ............. | G01S 13/88 |

OTHER PUBLICATIONS

Taiwanese Office Action dated Jul. 5, 2021 for Taiwanese Patent Application No. 109144803, 10 pages.

*Primary Examiner* — Bernarr E Gregory (74) *Attorney, Agent, or Firm* — Demian K. Jackson; Jackson IPG PLLC (57) ABSTRACT

A vital-sign radar sensor uses wireless internet signals to detect vital signs. It includes a first and second demodulation unit to demodulate an incident and reflected wireless internet signal with an injection-locked oscillator into a first and second demodulated signal, respectively. The combined use of the first and second demodulated signals can eliminate the influence of communication modulation on the extraction process of a Doppler shift due to vital signs. Moreover, the vital-sign radar sensor is a receive-only device so that it won't cause interference to ambient wireless communication networks.

9 Claims, 6 Drawing Sheets

(56) References Cited

U.S. PATENT DOCUMENTS

| | | | | |
|---|---|---|---|---|
| 2020/0103493 A1* | 4/2020 | Wang | .................. | G01S 7/415 |
| 2021/0109208 A1* | 4/2021 | Horng | .................. | G01S 7/415 |
| 2021/0302558 A1* | 9/2021 | Peng | .................. | A61B 5/0507 |
| 2021/0341595 A1* | 11/2021 | Yu | .................. | G01S 7/352 |

* cited by examiner

VITAL-SIGN RADAR SENSOR USING WIRELESS INTERNET SIGNALS

FIELD OF THE INVENTION

This invention generally relates to a vital-sign radar sensor, and more particularly to a vital-sign radar sensor using wireless internet signals.

BACKGROUND OF THE INVENTION

Conventional Doppler radar transmits a wireless signal to a target and receives an echo signal from the target to detect vital signs (e.g. respiration and heartbeat) of the target by extracting the Doppler shift of the echo signal that is caused by the target's vital-sign movements relative to the radar. However, signal interference may occur in wireless communication networks when the radar transmits the wireless signal to the target. This problem can be avoided by using a passive Doppler radar which detects the target with an ambient wireless communication signal rather than with a specific radar signal. Nevertheless, by doing so, the extraction of the Doppler shift of the echo signal is difficult because of the influence of communication modulation. The prior arts use channel state information (CSI) or error vector magnitude (EVM) in communication systems to estimate the Doppler effect on the received wireless communication signal, also resulting in successful vital-sign detection of the target. However, these prior arts cannot measure the Doppler shift due to vital signs as quantitatively as can the conventional Doppler radar.

SUMMARY

The present invention uses a first and second demodulation unit to demodulate an incident and reflected wireless communication signal with an injection-locked oscillator (ILO) into a first and second demodulated signal, respectively, from which the Doppler shift can be extracted by canceling the modulation of the reflected wireless communication signal. As a result, the present invention can detect the Doppler shift due to vital signs with ambient wireless communication signals.

One aspect of the present invention provides a vital-sign radar sensor using wireless internet signals. The vital-sign radar sensor includes a first splitter, an injection-locked oscillator (ILO), a second splitter, a first demodulation unit, a receive antenna, a second demodulation unit and a processing unit. The first splitter receives and splits a wireless internet signal into two parts. The ILO is electrically connected to the first splitter to receive one part of the wireless internet signal for injection into the ILO and generates an ILO output signal accordingly. The second splitter is electrically connected to the ILO to receive and splits the ILO output signal into two parts. The first demodulation unit has a first RF (radio frequency) terminal and a first LO (local oscillator) terminal where the first RF terminal is electrically connected to the first splitter to receive the other part of the wireless internet signal, and the first LO terminal is electrically connected to the second splitter to receive one part of the ILO output signal. The first demodulation unit uses the ILO output signal as a LO signal to demodulate the wireless internet signal into a first demodulated signal. A reflected signal, which is the wireless internet signal reflected from a target, is received by the receive antenna as a detection signal. The second demodulation unit has a second RF terminal and a second LO terminal where the second RF terminal is electrically connected to the receive antenna to receive the detection signal, and the second LO terminal is electrically connected to the second splitter to receive the other part of the ILO output signal. The second demodulation unit also uses the ILO output signal as a LO signal to demodulate the detection signal into a second demodulated signal. The processing unit is electrically connected to the first and second demodulation units to receive the first and second demodulated signals and provided to extract vital signs of the target from the Doppler shift in the detection signal using the first and second demodulated signals.

The first and second demodulation units demodulate the incident and reflected wireless internet signals from two different receive channels into the first and second demodulated signals, respectively. The combined use of the first and second demodulated signals can eliminate the influence of communication modulation on the extraction process of the Doppler shift caused by vital signs of the target. Moreover, the vital-sign radar sensor of the present invention is a receive-only device so that it won't cause interference to ambient wireless communication networks.

DETAILED DESCRIPTION OF THE INVENTION

Figure 1:
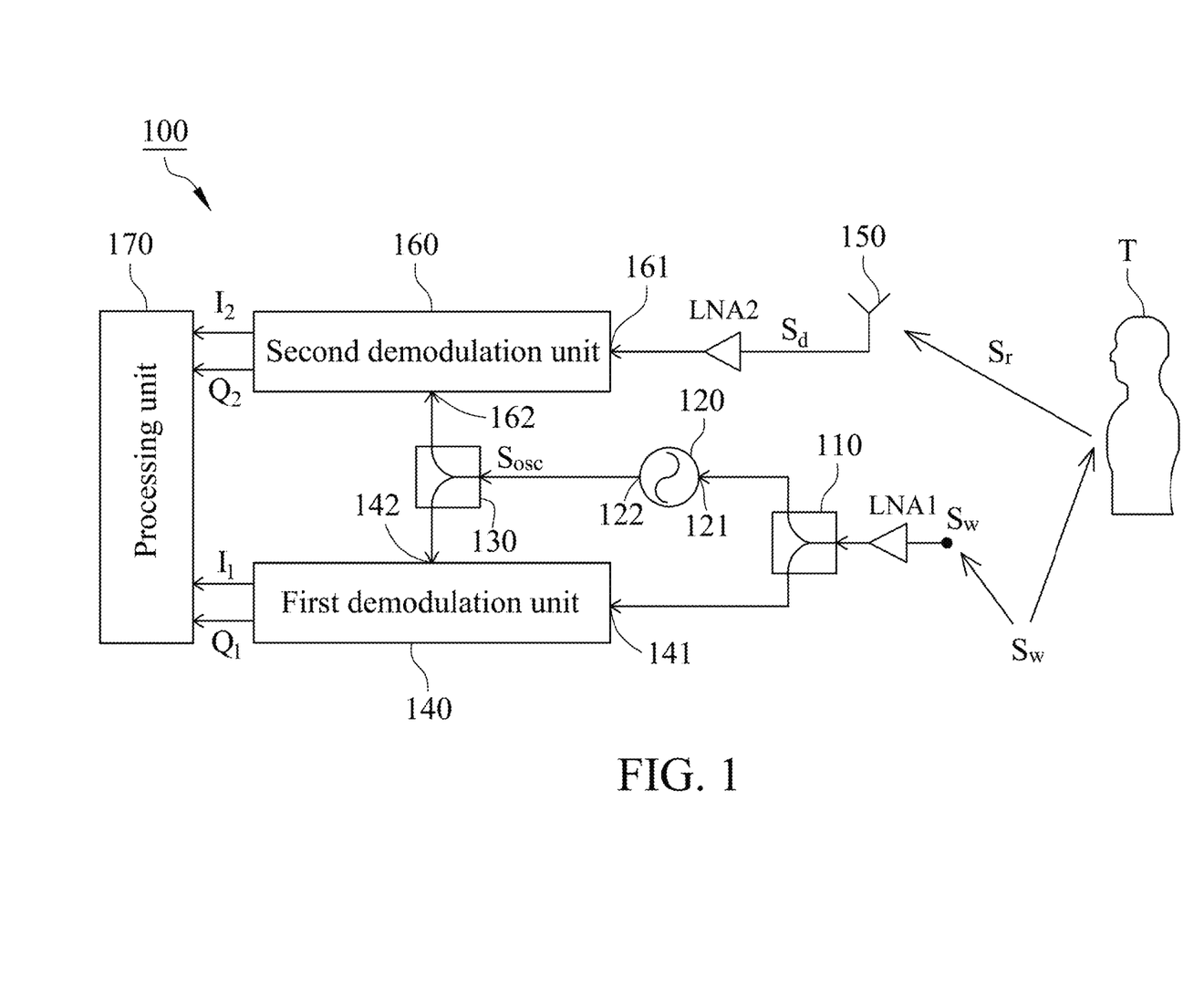
FIG. 1 is a circuit diagram illustrating a vital-sign radar sensor using wireless internet signals in accordance with one embodiment of the present invention.

FIG. 1 is a circuit diagram of a vital-sign radar sensor 100 using wireless internet signals in accordance with one embodiment of the present invention. It includes a first splitter 110, an injection-locked oscillator (ILO) 120, a second splitter 130, a first demodulation unit 140, a receive antenna 150, a second demodulation unit 160 and a processing unit 170.

The first splitter 110 receives a wireless internet signal $S_w$ from a first low-noise amplifier LNA1 and splits it into two parts. The wireless internet signal $S_w$ may be an uplink signal or a downlink signal from a wireless internet device that is received by the first splitter 110 via wire or wireless transmission. The wireless internet signal $S_w$ is also transmitted to a target T wirelessly, and a reflected signal $S_r$ from the target T is produced accordingly. The reflected signal $S_r$ includes a Doppler shift caused by vital signs of the target T and a modulation component of the wireless internet signal $S_w$.

The ILO 120 is electrically connected to the first splitter 110 to receive one part of the wireless internet signal $S_w$ via its injection port 121 and generates an ILO output signal $S_{osc}$ at an output port 122 of the ILO 120 under injection locking. In this embodiment, the ILO 120 is a voltage-controlled oscillator which receives a control signal via its frequency-tuning terminal (not shown) to adjust its free-running oscillation frequency close to the carrier frequency of the wireless internet signal $S_w$. This aids in injection-locking the ILO 120 to the wireless internet signal $S_w$.

The second splitter 130 is electrically connected to the output port 122 of the ILO 120 to receive the ILO output signal $S_{osc}$. The ILO output signal $S_{osc}$ is split by the second splitter 130 into two parts that are delivered to the first demodulation unit 140 and the second demodulation unit 160, respectively.

The first demodulation unit 140 has a first RF (radio frequency) terminal 141 and a first LO (local oscillator) terminal 142. The first RF terminal 141 is electrically connected to the first splitter 110 to receive the other part of the wireless internet signal $S_w$, and the first LO terminal 142 is electrically connected to the second splitter 130 to receive one part of the ILO output signal $S_{osc}$. The first demodulation unit 140 uses the ILO output signal $S_{osc}$ as a LO signal to demodulate the wireless internet signal $S_w$ into a first demodulated signal. In this embodiment, the first demodulation unit 140 is a quadrature demodulator, and therefore the first demodulated signal includes a first in-phase demodulated signal $I_1$ and a first quadrature-phase demodulated signal $Q_1$.

Figure 2:
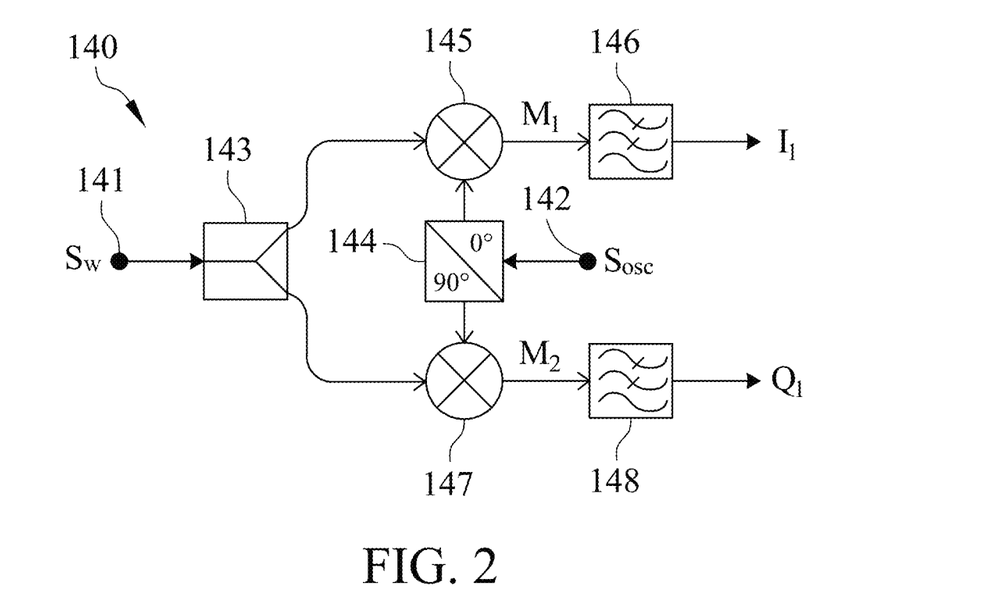
FIG. 2 is a circuit diagram illustrating a first demodulation unit of the vital-sign radar sensor in accordance with one embodiment of the present invention.

With reference to FIG. 2 which is a circuit diagram of the first demodulation unit 140 of this embodiment, the first demodulation unit 140 includes a third splitter 143, a first quadrature splitter 144, a first mixer 145, a first low-pass filter 146, a second mixer 147 and a second low-pass filter 148. The third splitter 143 is electrically connected to the first RF terminal 141 of the first demodulation unit 140 to receive and split the wireless internet signal $S_w$ into two parts. The first quadrature splitter 144 is electrically connected to the first LO terminal 142 of the first demodulation unit 140 to receive and split the ILO output signal $S_{osc}$ into a first in-phase LO signal and a first quadrature-phase LO signal. The first mixer 145 is electrically connected to the third splitter 143 and the first quadrature splitter 144 and provided to mix one part of the wireless internet signal $S_w$ with the first in-phase LO signal and output a first mixed signal $M_1$. The first low-pass filter 146 is electrically connected to the first mixer 145 and provided to remove high-frequency noise from the first mixed signal $M_1$ and output the first in-phase demodulated signal $I_1$. The second mixer 147 is electrically connected to the third splitter 143 and the first quadrature splitter 144 and provided to mix the other part of the wireless internet signal $S_w$ with the first quadrature-phase LO signal and output a second mixed signal $M_2$. The second low-pass filter 148 is electrically connected to the second mixer 147 and provided to remove high-frequency noise from the second mixed signal $M_2$ and output the first quadrature-phase demodulated signal $Q_1$.

As a result of injection-locking, the ILO output signal $S_{osc}$ is synchronized to the wireless internet signal $S_w$ and modulated with the phase of the modulation component of the wireless internet signal $S_w$ within the locking range of the ILO 120. Such a phase modulation is cancelled out in the mixing process of the wireless internet signal $S_w$ and the ILO output signal $S_{osc}$. Consequently, the quadrature demodulation of the wireless internet signal $S_w$ using the ILO output signal $S_{osc}$ as the LO signal produces the first demodulated signal with an amplitude and an out-of-locking-range phase of the modulation component of the wireless internet signal $S_w$. The first demodulated signal can be represented by the following equation:

$$I_1(t)+jQ_1(t)=A_m(t)e^{j\theta_r(t)}$$

where $I_1(t)$ is a time-domain expression of the first in-phase demodulated signal $I_1$, $Q_1(t)$ is a time-domain expression of the first quadrature-phase demodulated signal $Q_1$, $A_m(t)$ denotes the amplitude of the modulation component of the wireless internet signal $S_w$, and $\theta_r(t)$ denotes the out-of-locking-range phase of the modulation component of the wireless internet signal $S_w$.

With reference to FIG. 1, the receive antenna 150 receives the reflected signal $S_r$ from the target T as a detection signal $S_d$ which contains the Doppler shift caused by vital signs of the target T and the modulation component of the wireless internet signal $S_w$. The second demodulation unit 160 includes a second RF terminal 161 and a second LO terminal 162. The second RF terminal 161 is coupled to the receive antenna 150 via a second low-noise amplifier LNA2 to receive the detection signal $S_d$, and the second LO terminal 162 is electrically connected to the second splitter 130 to receive the other part of the ILO output signal $S_{osc}$. The second demodulation unit 160 uses the ILO output signal $S_{osc}$ as a LO signal to demodulate the detection signal $S_d$ into a second demodulated signal.In this embodiment, the second demodulation unit 160 is a quadrature demodulator, and therefore the second demodulated signal includes a second in-phase demodulated signal $I_2$ and a second quadrature-phase demodulated signal $Q_2$.

Figure 3:
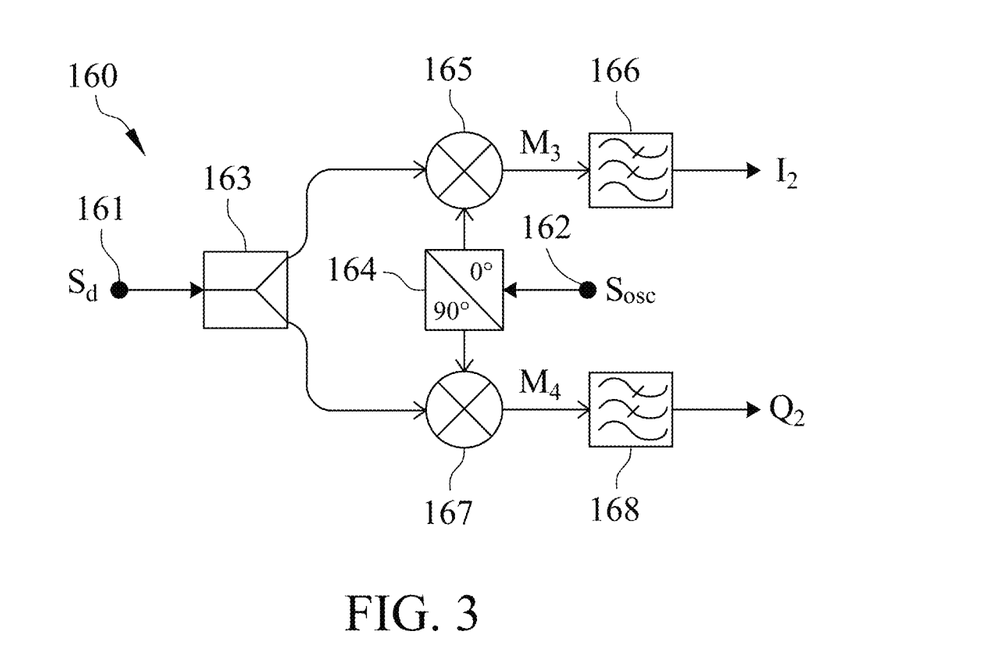
FIG. 3 is a circuit diagram illustrating a second demodulation unit of the vital-sign radar sensor in accordance with one embodiment of the present invention.

A circuit diagram of the second demodulation unit 160 of this embodiment is shown in FIG. 3. The second demodulation unit 160 includes a fourth splitter 163, a second quadrature splitter 164, a third mixer 165, a third low-pass filter 166, a fourth mixer 167 and a fourth low-pass filter 168. The fourth splitter 163 is electrically connected to the second RF terminal 161 of the second demodulation unit 160 to receive and split the detection signal $S_d$ into two parts. The second quadrature splitter 164 is electrically connected to the second LO terminal 162 of the second demodulation unit 160 to receive and split the ILO output signal $S_{osc}$ into a second in-phase LO signal and a second quadrature-phase LO signal. The third mixer 165 is electrically connected to the fourth splitter 163 and the second quadrature splitter 164 and provided to mix one part of the detection signal $S_d$ with the second in-phase LO signal and output a third mixed signal $M_3$. The third low-pass filter 166 is electrically connected to the third mixer 165 to remove high-frequency noise from the third mixed signal $M_3$ and output the second in-phase demodulated signal $I_2$. The fourth mixer 167 is electrically connected to the fourth splitter 163 and the second quadrature splitter 164 and provided to mix the other part of the detection signal $S_d$ with the second quadrature-phase LO signal and output a fourth mixed signal $M_4$. The fourth low-pass filter 168 is electrically connected to the fourth mixer 167 and provided to remove high-frequency noise from the fourth mixed signal $M_4$ and output the second quadrature-phase demodulated signal $Q_2$.

In a similar fashion to the quadrature demodulation of the wireless internet signal $S_w$, the quadrature demodulation of the detection signal $S_d$ using the ILO output signal $S_{osc}$ as the LO signal cancels out the phase modulation within the locking range of the ILO 120, resulting in the second demodulated signal given as the following equation:

$$I_2(t)+jQ_2(t)=\sigma A_m(t)e^{j(\theta_r(t)+\theta_d(t))}$$

where $I_2(t)$ is a time-domain expression of the second in-phase demodulated signal $I_2$, $Q_2(t)$ is a time-domain expression of the second quadrature-phase demodulated signal $Q_2$, $\sigma$ denotes an amplitude ratio of the detection signal $S_d$ to the wireless internet signal $S_w$ transmitted to the target T, and $\theta_d(t)$ denotes the Doppler shift caused by vital signs of the target T.

With reference to FIG. 1, the processing unit 170 is electrically connected to the first demodulation unit 140 and the second demodulation unit 160 to receive the first demodulated signal and the second demodulated signal. The processing unit 170 uses the first demodulated signal and the second demodulated signal to extract the Doppler shift caused by vital signs of the target T. In this embodiment, the first in-phase demodulated signal $I_1$ and the first quadrature-phase demodulated signal $Q_1$ of the first demodulated signal and the second in-phase demodulated signal $I_2$ and the second quadrature-phase demodulated signal $Q_2$ of the second demodulated signal are processed by the processing unit 170 to obtain the Doppler shift caused by vital signs of the target T according to the following equations:

$$I_3(t)+jQ_3(t)=\frac{I_2(t)+jQ_2(t)}{I_1(t)+jQ_1(t)}=\sigma e^{j\theta_d(t)}$$

$$\theta_d(t)=\tan^{-1}\frac{Q_3(t)}{I_3(t)}$$

where $I_3(t)$ and $Q_3(t)$ are a time-domain expression of the real and imaginary part, respectively, of the division of the second demodulated signal by the first demodulated signal, and $\theta_d(t)$ denotes the Doppler shift caused by vital signs of the target T.

Figure 4:
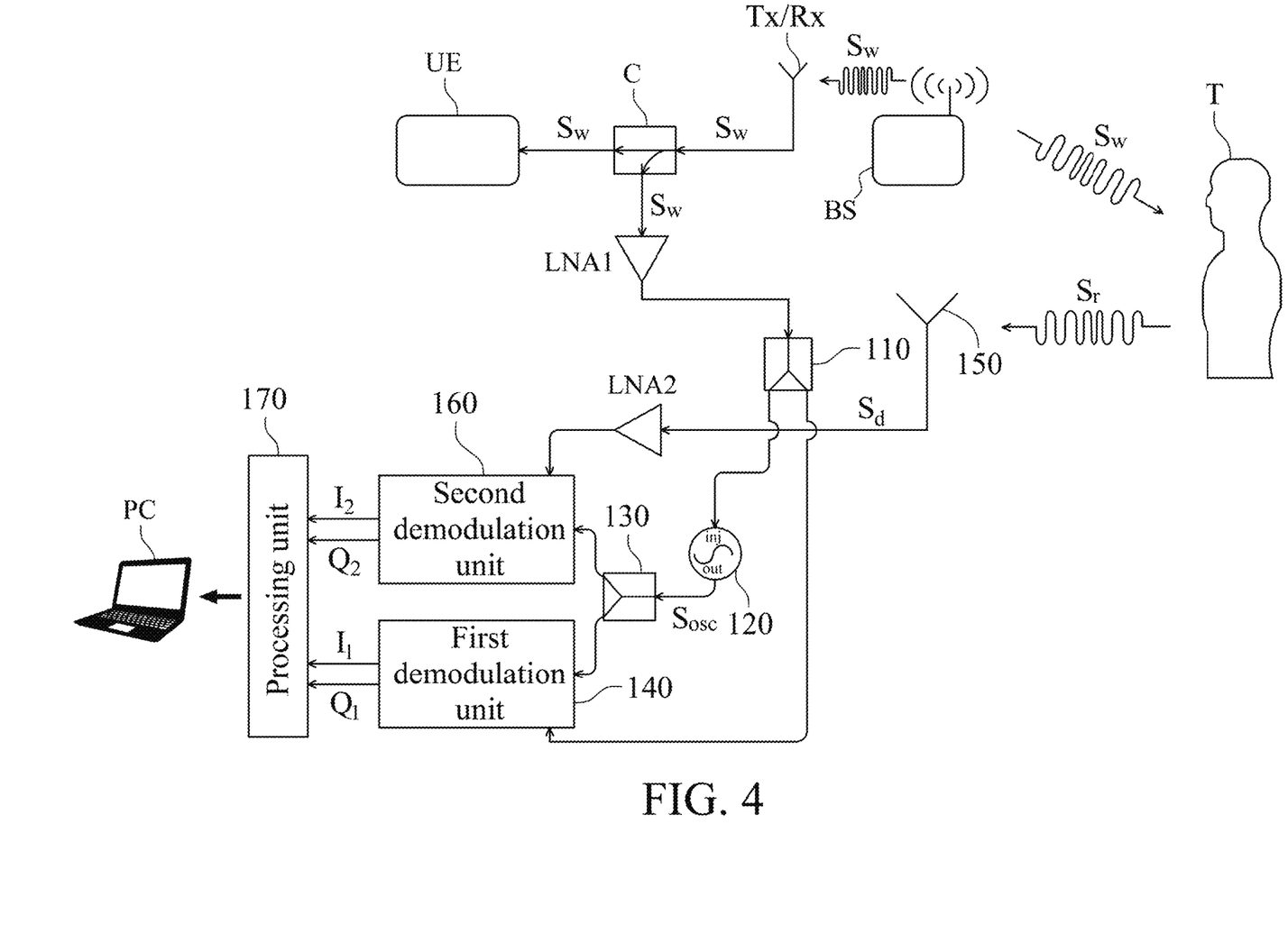
FIG. 4 is a circuit diagram illustrating the vital-sign sensor radar using a downlink signal from a base station in accordance with one embodiment of the present invention.
Figure 5:
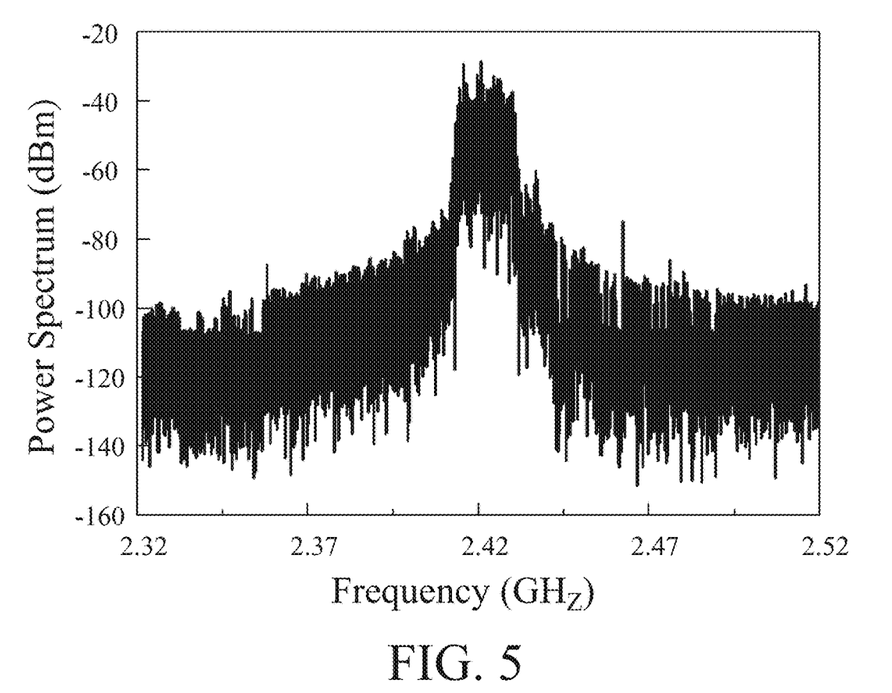
FIG. 5 shows the spectrum of the downlink signal from the base station in FIG. 4.
Figure 6:
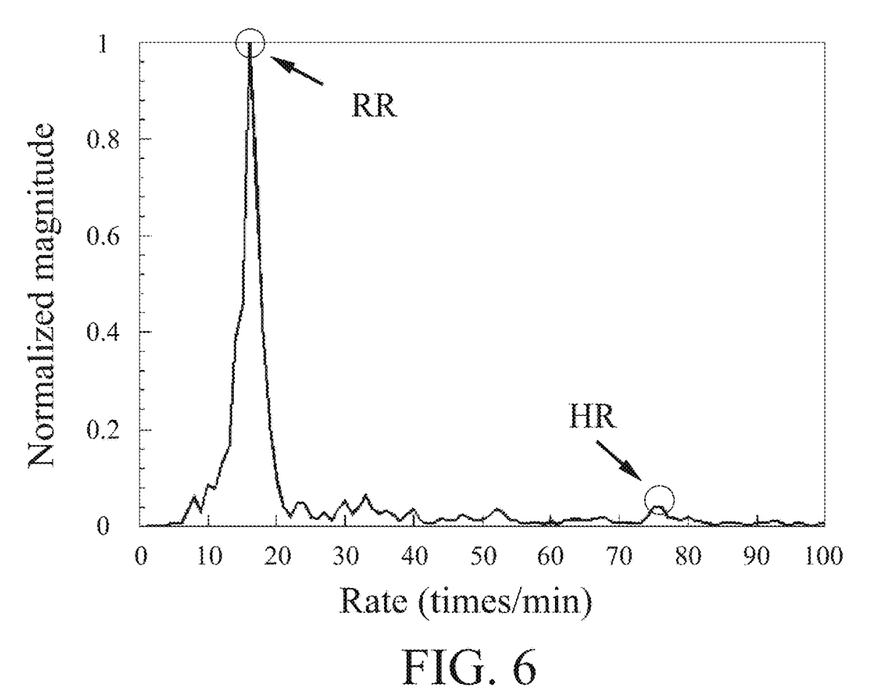
FIG. 6 shows the spectrum of Doppler shift obtained by the vital-sign radar sensor using the downlink signal in FIG. 4.

FIG. 4 is a circuit diagram of one embodiment of the present invention using a downlink signal from a base station BS as the wireless internet signal $S_w$. The base station BS transmits the wireless internet signal $S_w$ to the target T and a user equipment UE via a transceiver antenna Rx/Tx and a coupler C. Moreover, the coupler C couples a part of the wireless internet signal $S_w$, which is the downlink signal, to the first splitter 110 via the first low-noise amplifier LNA1. The reflected signal $S_r$ from the target T is received by the receive antenna 150 as the detection signal $S_d$. The Doppler shift caused by vital signs of the target T can be obtained through the subsequent processes of injection-locking, quadrature demodulation and Doppler extraction using the wireless internet signal $S_w$ and the detection signal $S_d$. Finally, the vital sign frequencies of the target T are identified in the spectrum of the extracted Doppler shift and displayed on a personal computer PC. FIG. 5 shows the spectrum of the downlink signal used as the wireless internet signal $S_w$. FIG. 6 displays the spectrum of the extracted Doppler shift where the respiration and heart rates are found as 16 and 76 times per minute, respectively.

Figure 7:
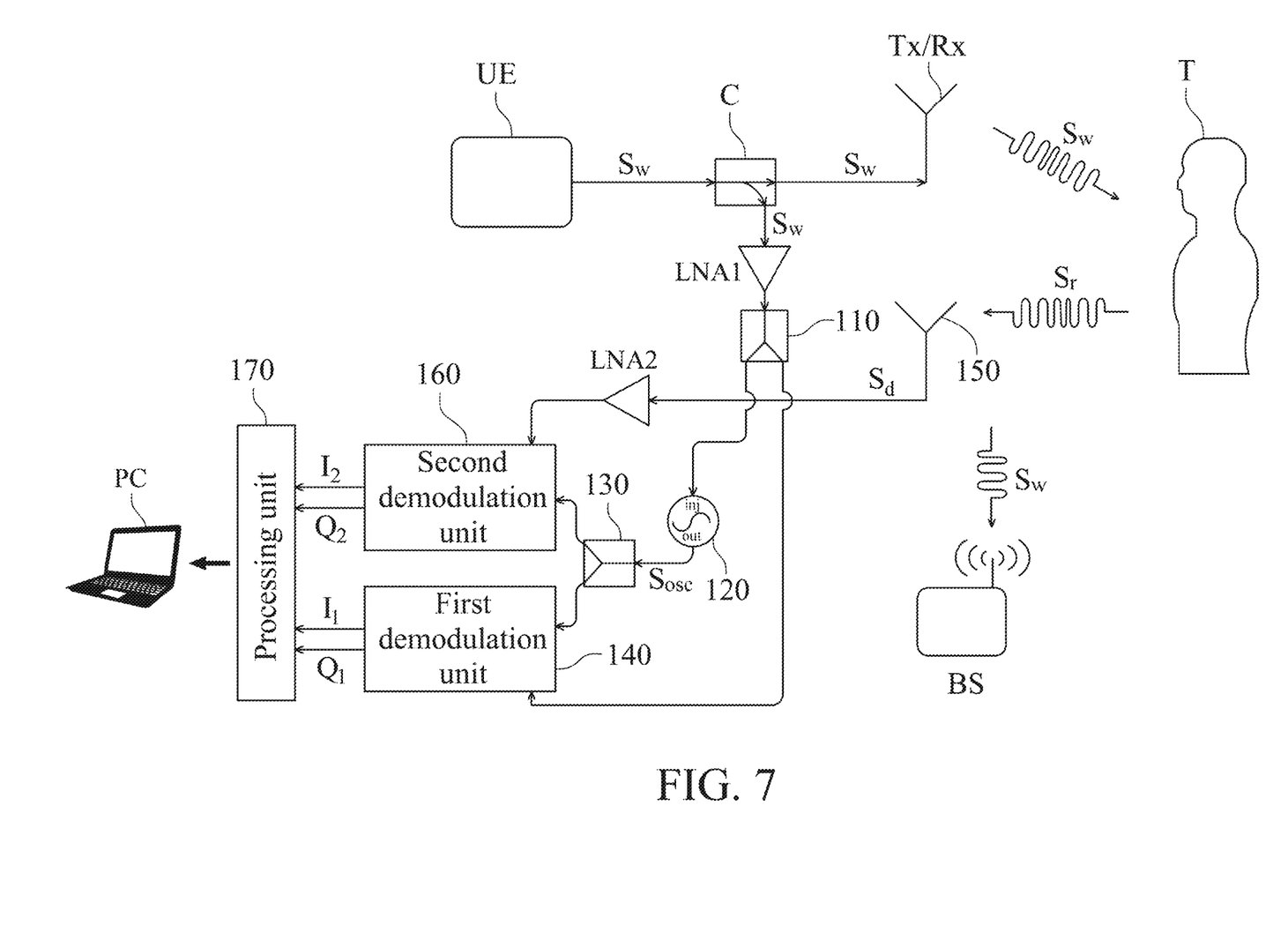
FIG. 7 is a circuit diagram illustrating the vital-sign radar sensor using an uplink signal from a user equipment in accordance with one embodiment of the present invention.
Figure 8:
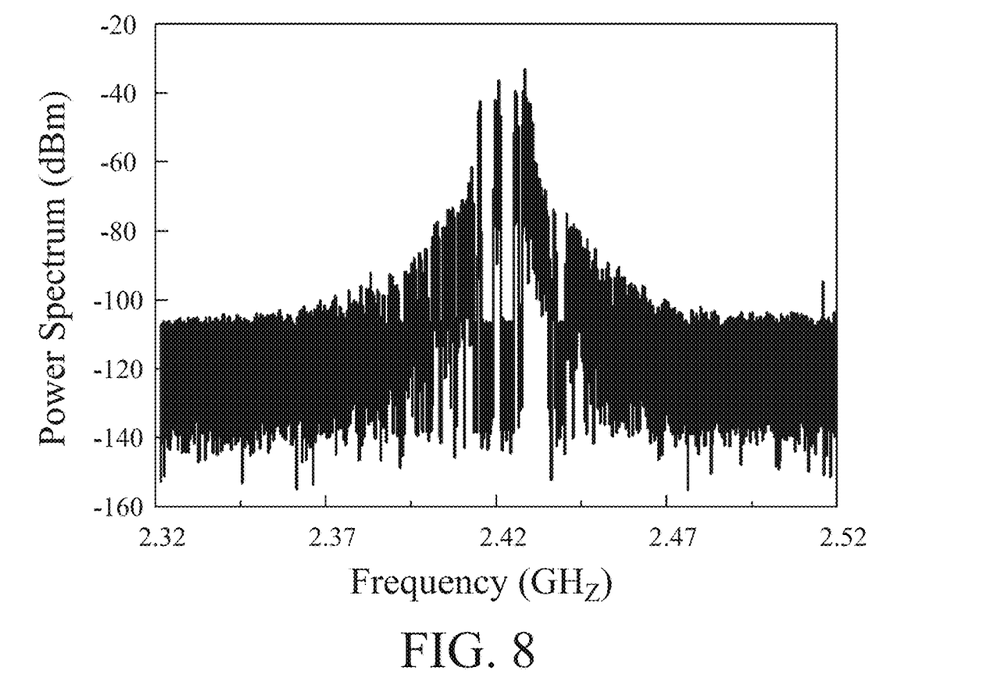
FIG. 8 shows the spectrum of the uplink signal from the user equipment in FIG. 7.
Figure 9:
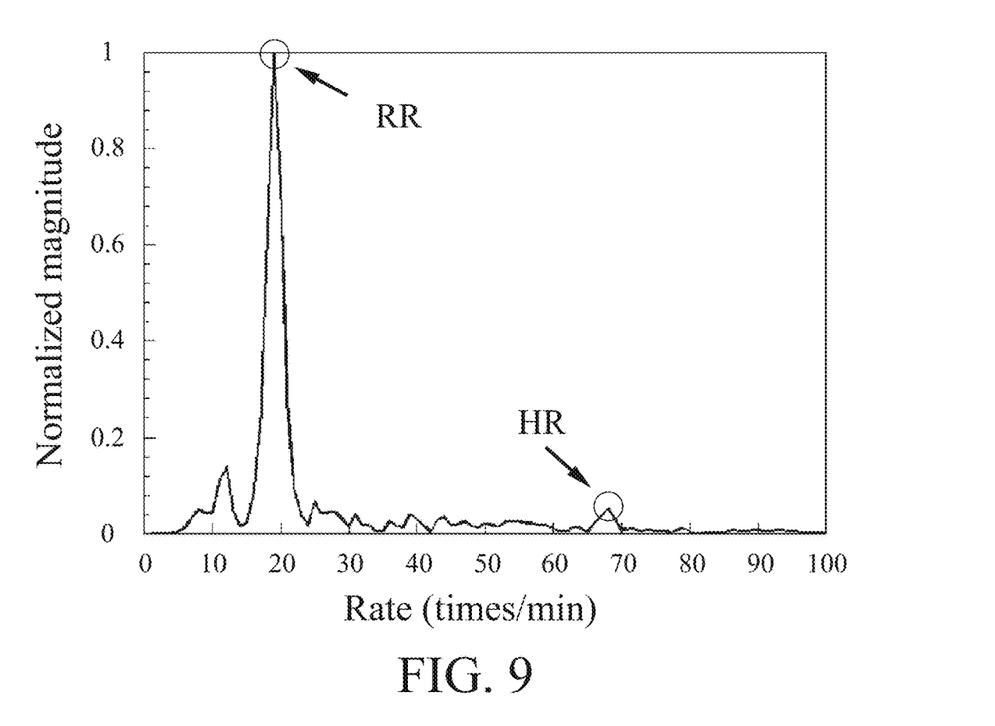
FIG. 9 shows the spectrum of Doppler shift obtained by the vital-sign radar sensor using the uplink signal in FIG. 7.

FIG. 7 is another circuit diagram of one embodiment of the present invention using the uplink signal from the user equipment UE as the wireless internet signal $S_w$. The user equipment UE transmits the wireless internet signal $S_w$ to the target T and the base station BS via the transceiver antenna Tx/Rx. Moreover, the coupler C couples a part of the wireless internet signal $S_w$, which is the uplink signal, to the first splitter 110 via the first low-noise amplifier LNA1. The reflected signal $S_r$ from the target T is received by the receive antenna 150 as the detection signal $S_d$. The wireless internet signal $S_w$ and the detection signal $S_d$ are provided for the subsequent processes of injection-locking, quadrature demodulation and Doppler extraction to obtain the Doppler shift resulting from vital signs of the target T. Finally, the vital sign frequencies of the target T are identified in the spectrum of the extracted Doppler shift and displayed on the personal computer PC. FIG. 8 shows the spectrum of the uplink signal used as the wireless internet signal $S_w$. FIG. 9 displays the spectrum of the extracted Doppler shift where the respiration and heart rates are found as 19 and 68 times per minute, respectively.

Note that, in the above two scenarios, the wireless communication between the base station BS and the user equipment UE is not affected during the vital-sign detection period.

The first and second demodulation units 140 and 160 of the present invention are provided to demodulate the incident and reflected wireless internet signals $S_w$ from two different receive channels into the first and second demodulated signals, respectively. The combined use of the first and second demodulated signals can eliminate the influence of communication modulation on the extraction process of the Doppler shift caused by vital signs of the target T. Moreover, the vital-sign radar sensor 100 of the present invention is a receive-only device so that it won't cause interference to ambient wireless communication networks.

While this invention has been particularly illustrated and described in detail with respect to the preferred embodiments thereof, it will be clearly understood by those skilled in the art that is not limited to the specific features shown and described and various modified and changed in form and details may be made without departing from the spirit and scope of this invention.

What is claimed is:

1. A vital-sign radar sensor comprising:
a first splitter configured to receive and split a wireless internet signal into two parts;
an injection-locked oscillator (ILO) electrically connected to the first splitter configured to receive and be injection-locked with one part of the wireless internet signal and configured to generate an ILO output signal;
a second splitter electrically connected to the ILO and configured to receive and split the ILO output signal into two parts;
a first demodulation unit including a first RF (radio frequency) terminal and a first LO (local oscillator) terminal, the first RF terminal is electrically connected to the first splitter and configured to receive the other part of the wireless internet signal, the first LO terminal is electrically connected to the second splitter and configured to receive one part of the ILO output signal, the first demodulation unit is configured to demodulate the wireless internet signal using the ILO output signal as a LO signal and output a first demodulated signal;
a receive antenna configured to receive a reflected signal from a target as a detection signal;
a second demodulation unit including a second RF terminal and a second LO terminal, the second RF terminal is electrically connected to the receive antenna and configured to receive the detection signal, the second LO terminal is electrically connected to the second splitter and configured to receive the other part of the ILO output signal, the second demodulation unit is configured to demodulate the detection signal using the ILO output signal as a LO signal and output a second demodulated signal; and a processing unit electrically connected to the first and second demodulation units, configured to receive the first and second demodulated signals and configured to extract a Doppler shift in the detection signal using the first and second demodulated signals.

2. The vital-sign radar sensor in accordance with claim 1, wherein the first and second demodulation units are quadrature demodulators, the first demodulated signal output from the first demodulation unit includes a first in-phase demodulated signal and a first quadrature-phase demodulated signal, and the second demodulated signal output from the second demodulation unit includes a second in-phase demodulated signal and a second quadrature-phase demodulated signal.

3. The vital-sign radar sensor in accordance with claim 2, wherein the first demodulation unit includes a third splitter, a first quadrature splitter, a first mixer, a first low-pass filter, a second mixer and a second low-pass filter, the third splitter is electrically connected to the first RF terminal of the first demodulation unit and configured to receive and split the wireless internet signal into two parts, the first quadrature splitter is electrically connected to the first LO terminal of the first demodulation unit and configured to receive and split the ILO output signal into a first in-phase LO signal and a first quadrature-phase LO signal, the first mixer is electrically connected to the third splitter and the first quadrature splitter, configured to mix one part of the wireless internet signal with the first in-phase LO signal and configured to output a first mixed signal, the first low-pass filter is electrically connected to the first mixer, configured to remove high-frequency noise from the first mixed signal and configured to output the first in-phase demodulated signal, the second mixer is electrically connected to the third splitter and the first quadrature splitter, configured to mix the other part of the wireless internet signal with the first quadrature-phase LO signal and configured to output a second mixed signal, the second low-pass filter is electrically connected to the second mixer, configured to remove high-frequency noise from the second mixed signal and configured to output the first quadrature-phase demodulated signal.

4. The vital-sign radar sensor in accordance with claim 2, wherein the second demodulation unit includes a fourth splitter, a second quadrature splitter, a third mixer, a third low-pass filter, a fourth mixer and a fourth low-pass filter, the fourth splitter is electrically connected to the second RF terminal of the second demodulation unit and configured to receive and split the detection signal into two parts, the second quadrature splitter is electrically connected to the second LO terminal of the second demodulation unit and configured to receive and split the ILO output signal into a second in-phase LO signal and a second quadrature-phase LO signal, the third mixer is electrically connected to the fourth splitter and the second quadrature splitter, configured to mix one part of the detection signal with the second in-phase LO signal and configured to output a third mixed signal, the third low-pass filter is electrically connected to the third mixer, configured to remove high-frequency noise from the third mixed signal and configured to output the second in-phase demodulated signal, the fourth mixer is electrically connected to the fourth splitter and the second quadrature splitter, configured to mix the other part of the detection signal with the second quadrature-phase LO signal and configured to output a fourth mixed signal, the fourth low-pass filter is electrically connected to the fourth mixer, configured to remove high-frequency noise from the fourth mixed signal and configured to output the second quadrature-phase demodulated signal.

5. The vital-sign radar sensor in accordance with claim 2, wherein the processing unit is configured to extract the Doppler shift caused by vital signs of the target using the first in-phase demodulated signal and the first quadrature-phase demodulated signal of the first demodulated signal and the second in-phase demodulated signal and the second quadrature-phase demodulated signal of the second demodulated signal.

6. The vital-sign radar sensor in accordance with claim 5, wherein the Doppler shift is obtained according to the following equations:

$$I_1(t) + jQ_1(t) = A_m(t)e^{j\theta_r(t)}$$

$$I_2(t) + jQ_2(t) = \sigma A_m(t)e^{j(\theta_r(t)+\theta_d(t))}$$

$$I_3(t) + jQ_3(t) = \frac{I_2(t) + jQ_2(t)}{I_1(t) + jQ_1(t)} = \sigma e^{j\theta_d(t)}$$

$$\theta_d(t) = \tan^{-1}\frac{Q_3(t)}{I_3(t)}$$

where $I_1(t)$ is a time-domain expression of the first in-phase demodulated signal, $Q_1(t)$ is a time-domain expression of the first quadrature-phase demodulated signal, $A_m(t)$ is an amplitude of the modulation component of the wireless internet signal, $\theta_r(t)$ is an out-of-locking-range phase of the modulation component of the wireless internet signal, $\sigma$ is an amplitude ratio of the detection signal to the wireless internet signal transmitted to the target, $I_2(t)$ is a time-domain expression of the second in-phase demodulated signal, $Q_2(t)$ is a time-domain expression of the second quadrature-phase demodulated signal, $I_3(t)$ and $Q_3(t)$ are a time-domain expression of the real and imaginary part, respectively, of the division of the second demodulated signal by the first demodulated signal, and $\theta_d(t)$ is a time-domain expression of the Doppler shift.

7. The vital-sign radar sensor in accordance with claim 1, wherein the wireless internet signal is a downlink signal from a base station or an uplink signal from a user equipment, and the first splitter is configured to receive the wireless internet signal via wire or wireless transmission.

8. The vital-sign radar sensor in accordance with claim 7 further comprising a coupler and a transceiver antenna, wherein the transceiver antenna is configured to receive the wireless internet signal which is the downlink signal from the base station, the coupler is electrically connected to the user equipment and the transceiver antenna and configured to receive and split the wireless internet signal into two parts, one part of the wireless internet signal is configured to be delivered to the user equipment, and the other part of the wireless internet signal is configured to be delivered to the first splitter.

9. The vital-sign radar sensor in accordance with claim 7 further comprising a coupler and a transceiver antenna, wherein the coupler is electrically connected to the user equipment and the transceiver antenna and configured to receive and split the wireless internet signal which is the uplink signal from the user equipment into two parts, one part of the wireless internet signal is configured to be delivered to the transceiver antenna for transmission to the target and the base station, and the other part of the wireless internet signal is configured to be delivered to the first splitter.

* * * * *